United States Patent
Ueno et al.

(10) Patent No.: US 9,850,535 B2
(45) Date of Patent: Dec. 26, 2017

(54) NUCLEIC ACID DETECTION METHOD, DETECTION PROBE, DETECTION PROBE SET, AND NUCLEIC ACID QUANTIFICATION METHOD

(71) Applicants: The University of Tokyo, Bunkyo-ku, Tokyo (JP); Nikon Corporation, Chiyoda-ku, Tokyo (JP)

(72) Inventors: Taro Ueno, Tokyo (JP); Takashi Funatsu, Tokyo (JP); Takanori Ichiki, Tokyo (JP); Hirofumi Shiono, Fujisawa (JP)

(73) Assignees: The University of Tokyo, Tokyo (JP); Nikon Corporation, Tokyo (JP)

( * ) Notice: Subject to any disclaimer, the term of this patent is extended or adjusted under 35 U.S.C. 154(b) by 276 days.

(21) Appl. No.: 14/510,282

(22) Filed: Oct. 9, 2014

(65) Prior Publication Data
US 2015/0051105 A1 Feb. 19, 2015

Related U.S. Application Data

(63) Continuation of application No. PCT/JP2013/057410, filed on Mar. 15, 2013.

(30) Foreign Application Priority Data

Apr. 12, 2012 (JP) ................. 2012-091088

(51) Int. Cl.
*C12Q 1/68* (2006.01)
*C07H 21/00* (2006.01)
*C12P 19/34* (2006.01)

(52) U.S. Cl.
CPC ......... *C12Q 1/6876* (2013.01); *C12Q 1/6834* (2013.01); *C12Q 1/6837* (2013.01); *C12Q 2600/178* (2013.01)

(58) Field of Classification Search
CPC ............ C12C 1/68; C07H 21/00; C12P 19/34
See application file for complete search history.

(56) References Cited

U.S. PATENT DOCUMENTS 4,988,617 A * 1/1991 Landegren ........... C12Q 1/6827
                                                    435/6.11
6,235,502 B1 * 5/2001 Weissman ............ C12Q 1/6827
                                                    435/6.1

(Continued)

FOREIGN PATENT DOCUMENTS

WO    WO 2008/052774 A2    5/2008
WO    WO 2009/015359 A2    1/2009

OTHER PUBLICATIONS

Landegren et al., A ligase-Mediated Gene Detection Technique. Science241 :14077 (Aug. 26, 1988).*

(Continued)

*Primary Examiner* — Ethan C Whisenant
(74) *Attorney, Agent, or Firm* — Foley & Lardner LLP

(57) ABSTRACT

A method for detecting a target nucleic acid, comprising: (a) contacting a nucleic acid sample comprising a target nucleic acid, comprising a first portion and a second portion, with: (i) a detection probe, wherein the detection probe is labeled with a labeling substance and comprises a nucleic acid sequence that forms a stem-loop structure and having a 5' protruding end or a 3' protruding end that is capable of hybridizing to the second portion, and (ii) a capture probe comprising a nucleic acid sequence capable of hybridizing to the first portion, wherein the capture probe is immobilized to a substrate, under conditions to form a target nucleic acid-detection probe-capture probe complex by hybridizing the second portion to the detection probe and hybridizing the first portion to the capture probe; (b) ligating a first end of the detection probe with an end of the target nucleic acid and ligating a second end of the detection probe with an end of (Continued)

the capture probe; and (c) detecting the labeling substance of the nucleic acid-detection probe-capture probe complex formed on the substrate.

14 Claims, 8 Drawing Sheets

(56) References Cited

U.S. PATENT DOCUMENTS

| | | | | |
|---|---|---|---|---|
| 6,403,319 | B1* | 6/2002 | Lizardi | C07K 14/70578 435/6.1 |
| 7,125,660 | B2* | 10/2006 | Stanton | C12Q 1/6825 435/4 |
| 8,551,697 | B1* | 10/2013 | Bashkirov | C12Q 1/6825 435/6.1 |
| 2006/0074041 | A1* | 4/2006 | Johnston | C07H 21/00 514/44 A |
| 2006/0216724 | A1* | 9/2006 | Christians | C12P 19/34 435/6.12 |
| 2007/0269825 | A1* | 11/2007 | Wang | C12Q 1/6858 435/5 |
| 2008/0166707 | A1* | 7/2008 | Han | C12Q 1/6827 435/6.14 |
| 2009/0246788 | A1* | 10/2009 | Albert | C12Q 1/6827 435/6.12 |
| 2009/0269771 | A1* | 10/2009 | Schroeder | C12Q 1/6827 435/6.12 |
| 2012/0015821 | A1* | 1/2012 | Raymond | C12N 15/1093 506/2 |
| 2013/0045885 | A1* | 2/2013 | Mohapatra | C12Q 1/6851 506/9 |
| 2013/0203123 | A1* | 8/2013 | Nelson | C12Q 1/6811 435/91.52 |
| 2013/0210008 | A1* | 8/2013 | Feitsma | C12Q 1/6837 435/6.11 |

OTHER PUBLICATIONS

Vester et al., LNA (Locked Nucleic Acid): High-Affinity Targeting of Complementary RNA and DNA. Biochemistry 43 (42) :13233 (2004).*
International Search Report dated Jun. 4, 2013, in PCT/JP2013/057410.
Written Opinion of the International Searching Authority dated Jun. 4, 2013, in PCT/JP2013/057410.
Chen et al., "Real-time quantification of microRNAs by stem-loop RT-PCR," Nucleic Acids Research, 2005, 33(20):e179, 1-9.
Mitchell et al., "Circulating microRNAs as stable blood-based markers for cancer detection," PNAS, Jul. 29, 2008, 105(30):10513-10518.
Supplementary European Search Report dated Nov. 3, 2015, in EP 13775821.5.
Office Action dated Feb. 14, 2017, in JP 2014-510089, with English translation.
Ueno et al., "Label-free quantification of miRNA using an enzymatic sandwich-hybridization based on DNA microarray," Summary of the 25th Symposium on Biomedical-Analytical Sciences, Aug. 8, 2012, 116-117, Y-5, with English translation.

* cited by examiner

Alexa647-D-probe, miR-141
(18copy/$\mu m^2$=1.2amol/spot)

```
SEQUENCE LISTING

<160> NUMBER OF SEQ ID NOS: 36

<210> SEQ ID NO 1
<211> LENGTH: 22
<212> TYPE: RNA
<213> ORGANISM: Homo sapiens

<400> SEQUENCE: 1
uaacacuguc ugguaaagau gg                                               22

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      capture probe1

<400> SEQUENCE: 2
accagacagt gttaacaaca acaacaacaa caaca                                 35

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      detect probe1-1

<400> SEQUENCE: 3
ctcaactggt gtcgtgg                                                     17

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      detect probe1-2

<400> SEQUENCE: 4
```

```
gtcggcaatt cagttgagcc atcttt                                          26

<210> SEQ ID NO 5
<211> LENGTH: 21
<212> TYPE: RNA
<213> ORGANISM: Homo sapiens

<400> SEQUENCE: 5
ugagaugaag cacuguagcu c                                               21

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      capture probe2

<400> SEQUENCE: 6
gtgcttcatc tcaacaacaa caacaacaac aaca                                 34

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      detect probe2-1

<400> SEQUENCE: 7
ctcaactggt gtcgtgg                                                    17

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      detect probe2-2

<400> SEQUENCE: 8
gtcggcaatt cagttgagga gctaca                                          26

<210> SEQ ID NO 9
<211> LENGTH: 22
<212> TYPE: RNA
<213> ORGANISM: Homo sapiens

<400> SEQUENCE: 9
uaacacuguc ugguaacgau gu                                              22

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      detect probe3-1

<400> SEQUENCE: 10
gtcggcaatt cagttgagac atcgtt                                          26

<210> SEQ ID NO 11
<211> LENGTH: 22
<212> TYPE: RNA
<213> ORGANISM: Homo sapiens
```

<400> SEQUENCE: 11
ugagguagua gguuguauag uu                                           22

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      X9 oligonucleotide

<400> SEQUENCE: 12
aacctactac ctcaacaaca acaacaacaa caaca                             35

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      X10 oligonucleotide

<400> SEQUENCE: 13
acctactacc tcaacaacaa caacaacaac aaca                              34

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      X11 oligonucleotide

<400> SEQUENCE: 14
ctcaactggt gtcgtgg                                                 17

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      X12 oligonucleotide

<400> SEQUENCE: 15
gtcggcaatt cagttgagaa ctatac                                       26

<210> SEQ ID NO 16
<211> LENGTH: 11
<212> TYPE: RNA
<213> ORGANISM: Homo sapiens

<400> SEQUENCE: 16
ugagguagua g                                                       11

<210> SEQ ID NO 17
<211> LENGTH: 11
<212> TYPE: RNA
<213> ORGANISM: Homo sapiens

<400> SEQUENCE: 17
guuguauagu u                                                       11

<210> SEQ ID NO 18

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aactatacaa c                                                              11

<210> SEQ ID NO 19
<211> LENGTH: 22
<212> TYPE: RNA
<213> ORGANISM: Homo sapiens

<400> SEQUENCE: 19
ugagguagua gauuguauag uu                                                  22

<210> SEQ ID NO 20
<211> LENGTH: 11
<212> TYPE: RNA
<213> ORGANISM: Homo sapiens

<400> SEQUENCE: 20
auuguauagu u                                                              11

<210> SEQ ID NO 21
<211> LENGTH: 22
<212> TYPE: RNA
<213> ORGANISM: Homo sapiens

<400> SEQUENCE: 21
ugagguagua gguugugugg uu                                                  22

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
aacctactac ctca                                                           14

<210> SEQ ID NO 23
<211> LENGTH: 8
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23 aactatac                                                                   8

<210> SEQ ID NO 24
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
acctactacc tca                                                            13
```

<210> SEQ ID NO 25
<211> LENGTH: 9
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25 aaccacaca                                                                  9

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
aactatacaa cctactacct ca                                                  22

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
aaccacacaa acctactacc tca                                                 23

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
aaccacacac ctactacctc a                                                   21

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate
<220> FEATURE:
<223> OTHER INFORMATION: 3' thiol 6-FAM

<400> SEQUENCE: 29
accagacagt gttaacaaca acaacaacaa caaca                                    35

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: 5' phosphate
<220> FEATURE:
<221> NAME/KEY: modified_base
<222> LOCATION: (18)..(18)
<223> OTHER INFORMATION: Alexa647-AminoC6-dA

<400> SEQUENCE: 30
ctcaactggt gtcgtggagt cggcaattca gttgagccat cttt        44

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate
<220> FEATURE:
<223> OTHER INFORMATION: 3' thiol 6-FAM

<400> SEQUENCE: 31
gtgcttcatc tcaacaacaa caacaacaac aaca        34

<210> SEQ ID NO 32
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate
<220> FEATURE:
<221> NAME/KEY: modified_base
<222> LOCATION: (18)..(18)
<223> OTHER INFORMATION: Alexa647-AminoC6-dA

<400> SEQUENCE: 32
ctcaactggt gtcgtggagt cggcaattca gttgaggagc taca        44

<210> SEQ ID NO 33
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate
<220> FEATURE:
<221> NAME/KEY: modified_base
<222> LOCATION: (18)..(18)
<223> OTHER INFORMATION: Alexa647-AminoC6-dA

<400> SEQUENCE: 33
ctcaactggt gtcgtggagt cggcaattca gttgagacat cgtt        44

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate
<220> FEATURE:
<223> OTHER INFORMATION: 3' thiol 6-FAM

<400> SEQUENCE: 34

```
aacctactac ctcaacaaca acaacaacaa caaca                              35

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate
<220> FEATURE:
<223> OTHER INFORMATION: 3' thiol 6-FAM

<400> SEQUENCE: 35
acctactacc tcaacaacaa caacaacaac aaca                               34

<210> SEQ ID NO 36
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate
<220> FEATURE:
<221> NAME/KEY: modified_base
<222> LOCATION: (18)..(18)
<223> OTHER INFORMATION: Alexa647-AminoC6-dA

<400> SEQUENCE: 36
ctcaactggt gtcgtggagt cggcaattca gttgagaact atac                    44
```

NUCLEIC ACID DETECTION METHOD, DETECTION PROBE, DETECTION PROBE SET, AND NUCLEIC ACID QUANTIFICATION METHOD

CROSS-REFERENCE TO RELATED APPLICATION

This is a Continuation Application of International Application No. PCT/JP2013/057410, filed Mar. 15, 2013, Filch claims priority to Japanese Patent Application No. 2012-091088 filed on Apr. 12, 2012. The contents of the aforementioned applications are incorporated herein by reference.

SEQUENCE LISTING

The instant application contains a Sequence Listing which has been submitted electronically in ASCII format and is hereby incorporated by reference in its entirety. Said ASCII copy, created on Oct. 30, 2014, is named 107929-0105_SL.txt and is 8,686 bytes in size.

TECHNICAL FIELD

The present invention relates to a nucleic acid detection method, detection probe, detection probe set, and nucleic acid quantification method.

BACKGROUND ART

Conventionally, DNA microarray targeting mRNA is widely used as a means of measuring the gene expression levels in cells. In the 21st century, it is reported that miRNA, Filch is a short-chain and a non-coding RNA, controls gene expression in vivo, and relationships between abnormal expression of miRNA and a variety of diseases such as the cancer have been elucidated. Based on these findings, development race of the DNA microarray targeting miRNA takes place.

Furthermore, the possibility of diagnosis of cancer in which blood test is simply conducted was shown since Mitchell et al, Proc. Nat, Acad. Sci. vol. 105, pp 10513-10518, 2008, showed that miRNA is circulating in the blood in 2008. Accordingly, it is expected that the market of DNA microarray targeting miRNA will rapidly expand in the near future.

On the other hand, quantitative PCR (qRT-PCR) method is widely put to practical use as a technique which quantifies miRNA by using a reverse transcription reaction to cDNA. The quantitative PCR method is a method which converts miRNA to cDNA by using a reverse transcriptase, and amplifies the cDNA, to estimate the amount of miRNA used as a template. The quantitative PCR method has a problem such that parallel processing for multiple samples and various miRNAs is difficult, since it is a method for measuring the amount of cDNA amplified to a certain amount by using PCR reaction, while quantitative capability is higher than that of DNA microarray.

The existing DNA microarrays targeting miRNA (hereinafter referred as miRNA targeting DNA microarrays) are obtained by arranging nucleic acid probes having gene sequences complementarily hybridizing to the objective miRNA a transparent substrate.

As the quantification method of miRNA using miRNA targeting DNA microarrays, for example, the following methods are exemplified. First, after extracting miRNA from a biological sample, fluorescently miRNA, then the labeled miRNA is added to the miRNA targeting DNA microarray to hybridize to the nucleic acid probe on the substrate. Then, after washing miRNA that is nonspecifically adsorbed to the substrate, the amount of miRNA is estimated based on the fluorescence intensity.

When preparing miRNA from a biological sample, total RNA is extracted from the biological sample and purified, then the total RNA including miRNA is fluorescently labeled, then the fluorescently labeled total RNA including fluorescently labeled miRNA is contacted with miRNA targeting DNA microarrays.

However, miRNA is susceptible to the effect of adsorption or decomposition during pipetting in the case such pretreatment step is complex, because the amount of miRNA in vivo, especially in blood, is 0.01% by mass among total RNA and very small. Furthermore, there is also a problem such that variations in fluorescent labeling index of each measurement arise to lower the reproducibility of the measurement results.

In addition, it is desired that all of the pretreatment steps will be fully automated to be able to be performed on the chip by using μ-TAS (Micro-Total Analysis Systems) in the future, since such hand working pretreatment is affected by the technology differences of scientists or clinical laboratory technicians. Here, the μ-TAS means the microfluidic device analyzing biological molecules on a single chip provided with a small flow path, reaction chamber and mixing chamber on the chip by using the MEMS (Micro Electro Mechanical Systems) technology. However, the fluorescently labeling method becomes a bottleneck as shown below, integration into full automation has not progressed.

The main methods of fluorescently labeling miRNA include a method of fluorescently labeling the base portion of miRNA directly, and a method of adding a fluorescently labeled nucleotide to the 3' end of miRNA using an enzyme such as T4 DNA ligase.

However, since all of nucleic acids are fluorescently labeled non-specifically by these methods, it is necessary to remove the unreacted fluorescent reagent and the like from the fluorescently pre-labeled target miRNA prior to hybridization to the nucleic acid probe on the substrate. Gel filtration chromatography is generally used to separate these, and it is necessary to accurately separate short miRNA whose length is about 22 bases from the unreacted fluorescent reagent. For example, in the case of separating by using the μ-TAS, a step of migrating a biological sample in an area filled with resin for a long distance is required, and it is extremely difficult to carry out the step in a chip with a limited space. Even if it is possible, in order to repeat the experiment continuously, it is required to flush the unreacted fluorescence reagent by washing for a long time, and it is not practical.

For the above problem, a sandwich-type microarray method which can detect miRNA without the separation process of the unreacted fluorescent dye has been devised in WO2008/052774.

As a first method of the sandwich-type microarray method, concretely, the following steps are exemplified. First, by dual partitioning nucleic acid probes having a sequence complementary to each miRNA 103 which comprises first portion 100 and second portion 101, capture probe 104 (Capture probe) and detection probe 105 (Detect probe) are generated. Then, a microarray is fabricated by arranging the capture probe 104 group having a sequence complementary to the first portion 100 of each miRNA 103 on the substrate 106 (see FIG. 5).

Then, after contacting each miRNA 103 with the fabricated microarray substrates (substrate 106), the tripartite of miRNA 103, capture probe 104 and detection probe 105 are hybridized by contacting a solution containing the detection probe 105 group having a sequence complementary to the second portion 101 of each miRNA 103 with the microarray substrate (substrate 106). It is not necessary to separate the unreacted detection probe 104 by such as chromatography since the detection probe 105 recognizes and binds to the second portion 101 of miRNA 103, and non-specific binding to the capture probe 104 does not occur.

However, in the first method described in WO2008/052774, each sequence complementary to mRNA 103 in one probe becomes about 10 bases since the nucleic acid probe having a sequence complementary to miRNA 103 is divided into two portions. As a result, the affinity of miRNA 103 and the nucleic acid probe is reduced, and it is difficult to accurately quantify miRNA 103 which exists in blood in only trace amounts. In addition, pre-miRNA (precursor of miRNA) of about 70 bases is contained in the biological sample. There is a fundamental problem in the first method of WO2008/052774, it is impossible to accurately quantify only miRNA having a gene expression control function, because pre-miRNA contains a sequence of a miRNA of about 22 bases, and the first method of WO2008/052774 cannot distinguish pre-miRNA and miRNA.

As a solution to this problem, in the second method described in WO2008/052774, further, a method for covalently bonding miRNA 103 and the nucleic acid probe using ligase has been proposed (see FIG. 6). However in the first method shown in FIG. 5, when ligase is used, there is a risk such that the same molecule miRNA 103 is detected more than once, since the capture probe 104 is covalently bonded to the detection probe 105 which hybridized with miRNA 103 then miRNA 103 is dissociated and binds to the other capture probe 104.

On the other hand, in the second method shown in FIG. 6, dissociation of miRNA 103 from the substrate 106 is prevented by further using two kinds of the bridging probes 107, 108 (c-bridge107, d-bridge108) thereby covalently bonding the capture probe 104, miRNA 103 and the detection probe 109 by ligation.

DISCLOSURE OF THE INVENTION

Problems to be Solved by the Invention

However, for example, in the second method described in Patent Document the signal is detected only when all of miRNA 103 and four kinds of probes collide with each other and five kinds of the molecules form a complex, and the operation is complicated and time consuming.

The present invention provides a method for detecting nucleic acid which is capable of detecting the nucleic acid, as well as a detection probe and a detection probe set used in the method for detecting nucleic acid.

Means of Solving the Problems

As a result of conducting extensive studies to achieve the aforementioned problems, the inventors of the present invention found that the problems can be solved by using a detection probe that forms a stem-loop structure. Embodiments of the present invention provide the following (1) to (19).

(1) A method for detecting a target nucleic acid, comprising:
(a) contacting a nucleic acid sample comprising a target nucleic acid, comprising a first portion and a second portion, with:
(i) a detection probe, wherein the detection probe is labeled with a labeling substance and comprises a nucleic acid sequence that forms a stem-loop structure and having a 5' protruding end or a 3' protruding end that is capable of hybridizing to the second portion, and
(ii) a capture probe comprising a nucleic acid sequence capable of hybridizing to the first portion, wherein the capture probe is immobilized to a substrate, under conditions to form a target nucleic acid-detection probe-capture probe complex by hybridizing the second portion to the detection probe and hybridizing the first portion to the capture probe;
(b) ligating a first end of the detection probe with an end of the target nucleic acid and ligating a second end of the detection probe with an end of the capture probe; and
(c) detecting the labeling substance of the nucleic acid-detection probe-capture probe complex formed on the substrate.

(2) The method for detecting a target nucleic acid according to (1), wherein the nucleic acid sample comprising the target nucleic acid is contacted with the detection probe in a solution.

(3) The method for detecting a target nucleic acid according to (1) or (2), wherein the target nucleic acid is contacted with the detection probe after the target nucleic acid is contacted with the capture probe.

(4) The method for detecting a target nucleic acid according to any one of (1) to (3), wherein the target nucleic acid is contacted with the capture probe after the target nucleic acid is contacted with the detection probe.

(5) The method for detecting a target nucleic acid according to any one of (1) to (4), wherein the method further comprises a step of quantifying the target nucleic acid by quantitatively detecting the labeling substance of the nucleic acid-detection probe-capture probe complex formed on the substrate.

(6) The method for detecting a target nucleic acid according to any one of (1) to (5), Wherein a plurality of detection probes is employed to detect a plurality of different target nucleic acids in the nucleic acid sample, wherein the detection probes are labeled with a labeling substance that is different for each different target nucleic acid detected.

(7) The method for detecting a target nucleic acid according to any one of (1) to (6), wherein the 5' end or the 3' end of the capture probe is immobilized to the substrate.

(8) The method for detecting a target nucleic acid according to any one of (1) to (7), wherein the target nucleic acid is contacted with a plurality of detection probes having varying base lengths and a plurality of capture probes having varying base lengths.

(9) The method for detecting a target nucleic acid according to any one of (1) to (8), Wherein step (a) and step (b) are performed simultaneously.

(10) The method for detecting a target nucleic acid according to any one of (1) to (9), wherein the capture probe and/or the detection probe contain a LNA (Locked Nucleic Acid) or a BNA (Bridged Nucleic Acid).

(11) A detection probe that hybridizes to a target nucleic acid comprising a first portion and a second portion, wherein the detection probe comprises:
a first stem forming portion and a second stem forming portion, wherein the first and second stem forming portions are complementary to each other;

a loop portion located between the first and second stem forming portions, wherein the loop portion is labeled with a labeling substance; and a 5' protruding end or a 3' protruding end, comprising a sequence capable of hybridizing to the second portion of the target nucleic acid.

(12) The detection probe according to (11), wherein a label of the loop portion is related to the nucleotide sequence of the second portion.

(13) The detection probe according to (11) or (12), wherein the target nucleic acid is miRNA.

(14) A detection probe set comprising a plurality of detection probes that can hybridize to a plurality of different target nucleic acids each comprising a first portion and a second portion, wherein the detection probes comprise:

a first stem forming portion and a second stem forming portion, wherein the first and second stem forming portions are complementary to each other;

a loop portion located between the first and second stem forming portions, wherein the loop portion is labeled with a labeling substances that s different for each different target nucleic acid to be detected; and a 5' protruding end or a 3' protruding end, comprising a sequence capable of hybridizing to the second portion of a target nucleic acid.

(15) The detection probe set according to (14) wherein the target nucleic acid is miRNA.

(16) The method for detecting a target nucleic acid according to any one of (1) to (10), wherein the target nucleic acid is a short chain RNA.

(17) The method for detecting a target nucleic acid according to any one of (1) to (10) and (16), wherein the target nucleic acid is miRNA.

(18) The method for detecting a target nucleic acid according to any one of (1) to (10), (16) and (17), wherein the first portion of the target nucleic acid is about 5 to 17 bases.

(19) The method for detecting a target nucleic acid according to any one of (1) to (10) and (16) to (18), wherein the second portion of the target nucleic acid is about 5 to 17 bases.

BRIEF DESCRIPTION OF THE DRAWINGS

FIG. 7 discloses SEQ ID NOS 26-27, 11, 11, 26, 28, 21 and 21, respectively, in order of appearance.

BEST MODE FOR CARRYING OUT THE INVENTION

<<Method for Detecting Nucleic Acids>>

Figure 1:
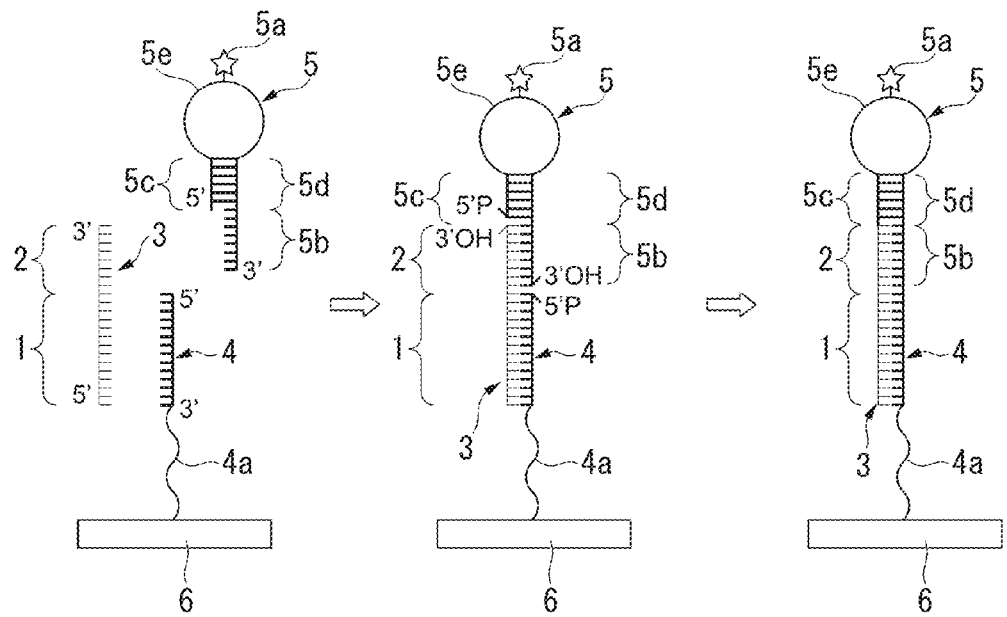
FIG. 1 is a schematic view of one embodiment of a method for quantifying nucleic acids in this embodiment.

The nucleic acid to be detected (target nucleic acid) is not particularly limited, short chain RNA such as miRNA or short chain mRNA generated by stopping transcription on the way is preferable and miRNA which exists in various types in vivo, and is involved in the regulation of gene expression is more preferable.

As an example, a method for quantifying nucleic acids of the present embodiment comprises, (a) a step of contacting a solution comprising:
   a nucleic acid sample containing miRNA comprising a first portion and a second portion, and
   a detection probe labeled with a labeling substance containing a sequence which forms a stem-loop structure and is capable of hybridizing to the second portion, and having 5' protruding end or 3' protruding end,
   with a substrate fixed with a capture probe containing a sequence capable of hybridizing to the first portion, (b) a step of forming the miRNA—the detection probe—the capture probe complex on the substrate by hybridizing the second portion to the detection probe and hybridizing the first portion to the capture probe, (c) a step of ligating an end of the detection probe and ends of the miRNA and the capture probe, (d) a step of quantitatively detecting the labeling substance of the miRNA—the detection probe—the capture probe complex formed on the substrate, and quantifying miRNA of the nucleic acid sample from a detection result.

Hereinafter, with reference to FIG. 1, each step in this embodiment will be described.

The step (a) is a step of contacting a solution comprising: a nucleic acid sample containing miRNA 3 comprising a first portion 1 and a second portion 2, and a detection probe 5 labeled with a labeling substance 5a containing a sequence 5b which forms a stem-loop structure and is capable of hybridizing to the second portion 2, and having 5' protruding end or 3' protruding end, with a substrate 6 fixed with a capture probe 4 containing a sequence capable of hybridizing to the first portion.

As shown in FIG. 1, miRNA 3 to be detected is divided into two portions, the first portion 1 and the second portion 2. That is to say, miRNA 3 comprises the first portion and the second portion.

The capture probe 4 and the detection probe 5 are capable of hybridizing to the first portion 1 and the second portion 2 of miRNA 3, respectively. Accordingly, the lengths of the first portion 1 and the second portion 2 are preferably 5 to 17 bases, and based on the viewpoint of the base number generated by dividing miRNA of about 22 bases into two portions, 7 to 15 bases are more preferable.

The lengths of these first portion 1 and second portion 2 are not particularly limited to the above base numbers, as long as the following two points are guaranteed. (1) The Tm values of the first portion 1 and the second portion 2 are near the optimum temperature of T4 DNA ligase (37° C.). (2) Sequence specificity is maintained. The above two points are affected by the GC content of the first portion 1 and the second portion 2 and existence of similar nucleic acids to the target miRNA. In the present embodiment, 5' portion of miRNA refers to the first portion 1 and 3' portion of miRNA refers to the second portion 7.

In the present invention and the specification of the present application, "capable of hybridizing" means that part of the capture probe and the detection probe used in the present invention hybridizes to the target nucleic acid (target miRNA) under the stringent conditions, and means that it does not hybridize to the nucleic acid molecule other than target nucleic acid (target miRNA). The "stringent conditions", for example, the conditions include those described in Molecular Cloning—A LABORATORY MANUAL THIRD EDITION (Sambrook et al, Cold Spring Harbor Laboratory Press).

The nucleic acid sample is not particularly limited, as long as the sample contains a nucleic acid, for example, when the method for quantifying nucleic acids of the present embodiment is used for diagnosis of cancer, the nucleic acid samples are preferably those obtained by extracting nucleic acids from a sample such as blood, lymph, cerebrospinal fluid, semen, saliva, urine, of a subject such as a person being identified onset of cancer, a person being suspected onset of cancer, or a patient being treated for cancer, etc. Nucleic acids extraction from these samples may be carried out by a conventional method such as using Trizol, but utilizing the method of extracting short chain RNA is preferred.

As described above, since the amount of miRNA in blood, is 0.01% by mass among total RNA and very small, miRNA enriched by fractionation from total RNA extracted from the sample may be used as a nucleic acid sample, in the present embodiment, a sample which is not fractionated may be used as a nucleic acid sample, since it is not necessary to label miRNA itself to be detected with a labeling substance.

The capture probe 4 contains a sequence capable of hybridizing to the first portion 1 of miRNA 3 in the 5' end region.

From the viewpoint of quantifying miRNA 3 with high accuracy, it is preferable that the capture probe 4 does not contain a sequence complementary to the second portion 2 of miRNA 3 so that the capture probe 4 does not hybridize to the second portion 2 of miRNA 3.

The capture probe 4 preferably has a spacer 4a at the 3' end which binds to the substrate 6, since molecular flexibility is required for hybridization of the capture probe 4 fixed to (immobilized to) the substrate 6 with miRNA 3. As the length of the spacer 4a is not particularly limited, 3 to 50 bases are preferable, 5 to 25 bases are more preferable. However, the bases used in the spacer, can be replaced with a linker such as PEG having the nearly equal length and softness. In such a case, the number of bases used for the spacer 4a may be 0 bases. The length of the capture probe 4 is not particularly limited, as long as the length is one required to function as a probe, but taking into account the number of bases of the first portion 1 and the spacer 4a, 3 to 50 bases are preferable, 5 to 40 bases are more preferable.

The capture probe 4 may be DNA or RNA, and it is not limited to natural or non-natural, as long as it has the similar function to RNA or DNA, and it may contain artificial nucleic acid such as PNA (peptide nucleic acid), LNA (Locked Nucleic Acid), BNA (Bridged Nucleic Acid), etc. The capture probe 4 preferably contact LNA or BNA since LNA and BNA has high affinity with the target miRNA 3 in comparison with DNA or RNA, and LNA and BNA is resistant to deoxyribonuclease or ribonuclease, and LNA and BNA can be a substrate for DNA ligase such as T4 DNA ligase.

Upon ligation in step (c), in this embodiment, the 5' end of the capture probe 4 is preferably phosphorylated by using the enzyme such as T4 polynucleotide kinase.

Moreover, in step (d), upon quantifying the miRNA 3-the detection probe 5-the capture probe 4 complex formed on the substrate 6, the capture probe 4 is preferably labeled with different types of the labeling substance from the labeling substance which is used for labeling the detection probe 5. The labeling substances used for labeling the capture probe 4 include similar substances used for labeling the detection probe 5 as described later.

The substrate 6 used for fixing the capture probe 4 includes a glass substrate, a silicon substrate, a plastic substrate, a metal substrate, and the like. The method for fixing the capture probe 4 on the substrate 6 includes a method for fixing the probe at a high density on the substrate by using a photolithographic technique, a method of fixing probe by spotting on a glass substrate, and the like.

In the case of using a photolithographic technique, it is possible to synthesize the capture probe 4 on the substrate 6. In the case of fixing the capture probe 4 by spotting, a solid phase binding site is preferably provided to the capture probe 4, and a recognition site for the solid phase binding site is preferably provided on the substrate 6.

The combinations of such solid phase binding site/the recognition site for the solid phase binding site include combinations of the solid phase binding site provided by modifying the capture probe 4 with a functional group such as an amino group, a formyl group, SH group, a succimidyl ester group, and the recognition site for the solid phase binding site provided by modifying the substrate 6 by surface treatment with a silane coupling agent having an amino group, a formyl group, an epoxy group, a maleimide group, and a combination using gold-thiol bond.

In addition, as another method for fixing the capture probe by spotting, a method of discharging capture probes having a silanol group on a glass substrate, arranging the capture probes, then covalently bonding the capture probes with a silane coupling reaction, is exemplified.

In this embodiment, the detection probe 5 contains a sequence 5b capable of hybridizing with the second portion 2 of miRNA 3 at the 3' terminal region.

From the viewpoint of accurate quantification of miRNA 3, it is preferable that the detection probe 5 does not contain a sequence complementary to the first portion 1 miRNA 3, so that it does not hybridize to the first portion 1 of miRNA 3.

The detection probe 5 forms a stem-loop structure. When there are complementary sequences in two separate regions within a molecule in a single-stranded nucleic acid, the stem-loop structure is formed by forming a complementary strand (stem structure) by the interaction between base pairs of nucleic acids, and by forming a loop structure of a sequence between the two regions. It is also referred to as a hairpin loop.

In this embodiment, the detection probe 5 comprises, from the 5' end, two stem portions 5c and 5d which form a complementary strand, a loop portion 5e which is a region between the two stem portions 5c and 5d, and a sequence 5b capable of hybridizing to the second portion 2. That is to say, the detection probe 5 has a 3' protruding end. The detection probe has a protruding end, and whether the protruding end of the detection probe is a 5' protruding end or 3' protruding end is determined by whether the capture probe is bound to the substrate via the 5' end or the 3' end of the capture probe.

The detection probe-miRNA-capture probe complex is not formed even if the capture probe forms a complex with pre-miRNA (precursor miRNA) containing a same base sequence region as miRNA, since the detection probe has a protruding end, and steric hindrance occurs. Therefore, according to this embodiment, it is possible to quantify the target miRNA with high accuracy, because pre-miRNA is not recognized, and only the target miRNA is recognized.

The length of the stem portion of the detection probe 5 is determined by the balance with the length of the loop portion, and it is not particularly limited as long as the detection probe 5 can stably form a stem-loop structure, but 3 to 50 bases are preferable, and 5 to 20 bases are tore preferable.

The length of the loop portion of the detection probe 5 is determined by the balance with the length of the stem portion, and it is not particularly limited as long as the detection probe 5 can stably form a stem-loop structure, but 3 to 200 bases are preferable, and 5 to 100 bases are more preferable.

The length of the detection probe 5 is not particularly limited as long as the detection probe 5 can stably form a stem-loop structure, and the length is one required to function as a probe. However, taking the base number of the second portion 2 and the base number necessary for the stem-loop structure formation into consideration, 14 to 200 bases are preferable, and 24 to 150 bases are more preferable.

The detection probe 5 may be DNA or RNA, and it is not limited to natural or non-natural, as long as it has the similar function to DNA or RNA, and it may contain artificial nucleic acid such as PNA (peptide nucleic acid), LNA (Locked Nucleic Acid), BNA (Bridged Nucleic Acid), etc. The detection probe 5 preferably contain LNA or BNA since LNA and BNA has high affinity with the target miRNA in comparison with DNA or RNA, LNA and BNA is resistant to deoxyribonuclease or ribonuclease, and LNA and BNA can be a substrate for DNA ligase such as T4 DNA ligase.

It is preferable that at least one of the capture probe 4 and the detection probe 5 contains LNA or BNA, and it is more preferable that both of the capture probe 4 and the detection probe 5 contains LNA or BNA.

Upon ligation in step (c), the 5' end of the detection probe 5 is preferably phosphorylated by using the enzyme such as T4 polynucleotide kinase.

The detection probe 5 is labeled with a labeling substance 5a. From the viewpoint of steric hindrance during the formation of the miRNA 3-detection probe 5-capture probe 4 complex described later, the labeling substance 5a is preferably bound to the loop portion 5e.

The labeling substances include, for example, fluorescent dye, fluorescent beads, quantum dots, biotin, antibody, antigen, energy absorbing materials, radioisotopes, chemiluminescent, enzyme, and the like.

The fluorescent dyes include, FAM (carboxyfluorescein), JOE (6-carboxy-4',5'-dichloro-2',7'-dimethoxyfluorescein), FITC (fluorescein isothiocyanate), TET (tetrachlorofluorescein), HEX (5'-hexachloro-fluorescein-CE phosphoramidite), Cy3, Cy5, Alexa568, Alexa647, and the like.

Since miRNA exists in only trace amounts among total RNA, labeling miRNA with high efficiency without fractionation is difficult. On the other hand, in the present embodiment, it is possible to quantitate miRNA with high sensitivity, since the detection probe which is labeled in advance is used.

If the capture probe 4 is labeled with a labeling substance, combination of a labeling substance for labeling the capture probe 4 and a labeling substance for labeling the detection probe 5, may be a combination by which FRET (Fluorescence Resonance Energy Transfer) cannot occur, and may be a combination by which FRET can occur.

The combination by which FRET cannot occur is preferred from the viewpoint that FRET efficiency is different by the sequence and length of the target miRNA. Even in the case of using a combination of the labeling substances by which FRET can occur, for example, can also be designed so that FRET between the labeling substances does not occur by labeling the near end of the capture probe to the substrate with FAM and labeling the farthest loop portion from the substrate of the detection probe with Alexa647.

In addition, the combination by which FRET can occur is preferable in view of being able to distinguish whether the detection probe is coupled to the capture probe or the detection probe is adsorbed to the substrate.

As a combination of the labeling substances by which FRET can occur, a combination of fluorescent dye excitation wavelength thereof is near 490 nm (for example, FITC, rhodamine green, Alexa (registered trademark) fluor 488, Body P FL, etc.) and fluorescent dye excitation wavelength thereof is near 540 nm (for example, TAMRA, tetramethyl rhodamine, Cy3), or a combination of fluorescent dye excitation wavelength thereof is near 540 nm and fluorescent dye excitation wavelength thereof is near 630 nm (for example, Cy5, or the like) is preferable.

In addition, in the present embodiment, the two probes, the capture probe and the detection probe recognize the first portion and the second portion of the target miRNA, respectively. For example, when miRNA is let-7a (5'-UGAGGUA-GUAG̲UUGUAUAGUU-3') (SEQ ID NO: 11), by setting the first portion of let-7a to 5'-UGAGGUAGUAG-3' (SEQ ID NO: 16) and setting the second portion of let-7a to 5'-G̲UUGUAUAGUU-3' (SEQ ID NO: 17) to produce the capture probe and the detection probe containing sequences capable of hybridizing to the first portion and the second portion, respectively. Here, in the detection probe, when setting a sequence that is capable of hybridizing to the second portion to 5'-AACTATACAAC̲-3' (SEQ ID NO: 18), let-7f (5'-UGAGGUAGUAGA̲UUGUAUAGUU-3') (SEQ ID NO: 19) in which the first base guanine is substituted with adenine in the second portion of let-7a, cannot form a covalent bond by ligation with detection probe.

Thus, according to this embodiment, it is possible to identify difference of one base in miRNA strictly, and to quantify the target miRNA with high accuracy.

Since the sequences of the first portions of the let-7a and let-7f are completely the same, when quantifying in parallel, both sequences hybridize to the same capture probe 4 on the microarray, each sequence forms the miRNA 3-detection probe 5-capture probe 4 complex. Therefore, a combined signal of both miRNAs is detected in the area, which may lead to erroneous results. For example, in Patent Document 1, this is a fatal problem.

The present inventors have found that it is possible to solve this problem by the following three points.

First, in the step (a), the solution preferably contains plural kinds of detection probes which are labeled with different kinds of labeling substances.

This is a method in which the detection probe (let-7a) and the detection probe (let-7f) which hybridize the second portions of let-7a and let-7f, respectively, are labeled with different kinds of labeling substances, thereby quantifying the each signal separately, A method of labeling the both probes in which fluorescent substances having different wavelengths, Alexa532 and Alexa647 are used as labeling substances is exemplified.

Secondly, in the step (a), the nucleic acid sample preferably contains plural kinds of miRNA having different sequence to be detected, and it is preferably selected that either 5' end or 3' end of the capture probe is fixed to (immobilized to) the substrate so as not to be the same sequence in the first portions of the plural kinds of miRNA.

This is a method in which the probes hybridizing to portions having different sequence among the similar miRNAs are used as the capture probes. When let-7a and let-7f are exemplified, 3' distal 5'-GUUGUAUAGUU-3' (SEQ ID NO: 17) and 5'-AUUGUAUAGUU-3' (SEQ ID NO: 20) having different sequences are set to the first portions, and 5' distal 5'-UGAGGUAGUAG-3' (SEQ ID NO: 16) having common sequence is set to the second portion. By inverting the position of the 5' end and 3' end shown in FIG. 1, it is possible to form the capture probe 4-detection probe 5-miRNA 3 complex in which the 5' end of the capture probe 4 is fixed on the substrate. In this case, sequence of the detection probe 5 for let-7a and let-7f is the same, the labeling substance to be labeled is also the same.

In addition, thirdly, in the step (a), the solution preferably contains a plurality of detection probes having different base lengths (varying base lengths), and a plurality of capture probes having different base lengths. For example, when two kinds of the target object miRNA are let-7a (5'-UGAGGUA-GUAGGUUGUAUAGUU-3') (SEQ ID NO: 11) and let-7b (5'-UGAGGUAGUAGGUUGUGUGGUU-3') (SEQ ID NO: 21), the capture probe (5'-AACCTACTACCTCA-3' (SEQ ID NO: 22); C-probe-let7a-D8) having 14 bases of complementary chain, and the detection probe (5'-AAC-TATAC-3' (SEQ ID NO: 23); D-probe-let7a-D8) having 8 bases of complementary chain are prepared as the probes for let-7a, and the capture probe (5'-ACCTACTACCTCA-3' (SEQ ID NO: 24); C-probe-let7b-D9) having 13 bases of complementary chain, and the detection probe (5'-AACCA-CACA-3' (SEQ ID NO: 25); D-probe-let7b-D9) having 9 bases of complementary chain are prepared as the probes for let-7b.

let-7a reacts only with the detection probe of 8 bases (D-probe-let7a-D8), thereby forming a binary complex, and further hybridizes to the capture probe of 14 bases (C-probe-let7a-D8), thereby forming a tertiary complex, then covalent bonds are formed by T4 DNA ligase.

Figure 7:
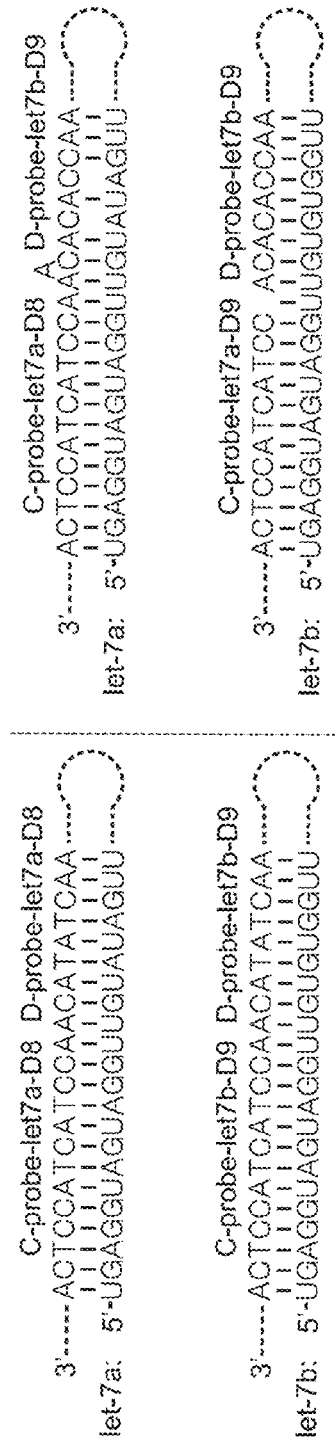
FIG. 7 is a schematic view of one embodiment of a method for quantifying nucleic acids in this embodiment.

On the other hand, the binary complex of let-7a and D-probe-let7a-D8 is possible to hybridize to the 13 bases of C-probe-let7b-D9 (However, the affinity is low since there is no stacking effect which occurs when the bases are laid side-by-side each other), it is not ligated since the one base nick exists as shown in the upper right of FIG. 7. The signal of the let-7a does not appear on the spot fixed with the C-probe-let7b-D9, because the signal will be 1/50,000 if ligation does not occur as described in Example 2 described below.

Vice versa, let-7b reacts only with the detection probe of 9 bases (D-probe-let7b-D9), thereby forming a binary complex, and further hybridizes to 13 bases of C-probe-let7b-D9), thereby forming a ternary complex, then covalent bonds are formed by T4 DNA ligase.

On the other hand, the binary complex of let-7b and D-probe-let7b-D9 is possible to hybridize to the 14 bases of C-probe-let7b-D9, it is not ligated since one base is surplus as shown in the bottom right of FIG. 7.

In Example 4 described below, it is confirmed that the signal is obtained when the capture probe and the detection probe is adjacent as shown in the upper left of FIG. 7, but the signal is not obtained at all when one base is deficient as shown in the upper right of FIG. 7. Concretely, as the capture probe fixed to the substrate, C-probe-let7a-D8 or C-probe-let7b-D9 was mixed with let-7a and D-probe-let7a-D8, and reacted in solution, then formation of ternary complex was confirmed by acrylamide gel electrophoresis. As a result, it has been confirmed that a ternary complex was formed only when C-probe-let7a-D8 is mixed with let-7a and D-probe-let7a-D8.

Thus, according to this embodiment, it is possible to strictly distinguish miRNA, and to quantify the target miRNA with high accuracy. In particular, when the abundances of two kinds of the target object miRNA are largely different, according to this embodiment, it is possible to accurately quantify the low-abundance target miRNA.

The liquid used for a solution comprising a nucleic acid sample contain miRNA 3, and the detection probe 5, includes buffers used for ordinary hybridization and the like.

The step (b) is a step in which the second portion 2 is hybridized to the detection probe 5, the first portion 1 is hybridized to the capture probe 4, thereby forming the miRNA 3-detection probe 5-capture probe 4 complex on the substrate 6.

In the step (b), since miRNA easily forms a steric structure, it is preferable that miRNA is heat-denatured by incubating at 95° C. for about 5 minutes, thereby enabling easily hybridizing to the probe.

The condition of hybridization is not particularly limited, it is preferable that hybridization is carried out under the stringent conditions from the viewpoint of the highly accurate quantification of miRNA although hybridization can be carried out under conventional conditions temperature, pH, salt concentration, buffer, etc., in consideration of the Tm value, etc., of each probe.

The stringent conditions include, for example, temperature conditions of about 30° C. (temperature conditions in which about 5° C. to 10° C. higher than the Tm of the probe sequence), salt concentration conditions of less than 1 M, and the like.

The step (c) is a step of ligating the end of the detection probe 5, miRNA 3 and the end of the capture probe 4.

In order to prevent the miRNA 3 which hybridized to the capture probe 4 and the detection probe 5, from dissociating from these probes, 5' end of the detection probe 5 and 3' end of miRNA 3 are ligated, and 3' end of the detection probe 5 and 5' end of the capture probe 4 are ligated.

By ligation, it is possible to prevent, from detecting a plurality of miRNA 3 in the step (e).

The enzyme used for ligation is preferably DNA ligase, for example, T4 DNA ligase is exemplified.

The step (b) and the step (c) may be carried out simultaneously. That is to say, hybridization and ligation may be carried out simultaneously.

Moreover, it is possible to ligate 3' end of the detection probe and 5' end of miRNA, and to ligate 5' end of the detection probe and the 3' end of the capture probe, in the case as other embodiments in which the capture probe and the substrate are bound via 5' end of the capture probe by using the detection probe having 5' protruding end because the 5" end of miRNA is phosphorylated during the biosynthesis.

By dividing the probe into two capture probe 4 and detection probe 5, the affinity of each probe and the target miRNA 3 is reduced slightly. However, it is possible to increase the affinity of each probe and the target miRNA 3 by that (1) the substrate 6 is bound to the capture probe 4 via the spacer 4*a* to impart a degree of molecular freedom to the capture probe 4, (2) the capture probe 4 and/or the detection probe 5 include LNA or BNA.

In order to remove those hybridized nonspecifically after the hybridization reaction is completed, it is preferable to wash the substrate 6. The method for was can be carried out under the usual conditions. From the viewpoint of quantifying miRNA with high accuracy, it is preferably carried out under the stringent conditions, for example, a method of washing several times by shaking the substrate 6 in a solution of low salt concentration is exemplified.

The step (d) is a step of quantitatively detecting the labeling substance 5a in the miRNA 3-detection probe 5-capture probe 4 complex formed on the substrate 6, and quantifying miRNA 3 in a nucleic acid sample from the detection result.

As described above, since the detection probe 5 is labeled with a labeling substance 5a, the labeling substance 5a in the miRNA 3-detection probe 5-capture probe 4 complex is quantitatively detected. In this case, it is preferable to prepare a standard curve by using known amounts of miRNA which is serially diluted, and to utilize the standard curve. It is possible to quantify miRNA 3 in a nucleic acid sample by using such detection results.

The detection method of the labeling substance in step (d) is not particularly limited, it can be carried out by using usual methods for detecting nucleic acids, for example, measuring the fluorescence intensity of the complex by using a nucleic acid microarray automatically detecting apparatus, and the like.

According to the method for quantifying miRNA in the present embodiment, since bridging probe conventionally required is unnecessary, the operation is simplified, in addition, since there is no need to label miRNA itself with a labeling substance, it is possible to quantify the target miRNA with high sensitivity.

Furthermore, according to the method for quantifying miRNA in the present embodiment, since the detection probe that forms a stem-loop structure is used, it is possible to detect the target miRNA without recognizing pre-miRNA.

<<Detection Probe and Detection Probe Set>>

Figure 2:
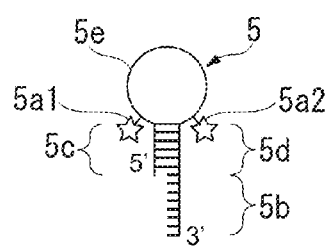
FIG. 2 is a schematic view of one embodiment of the detection probe in the embodiment.

As shown in FIG. 2, the detection probe of the present embodiment is a detection probe 5 used to detect a nucleic acid comprising a first portion and a second portion in a nucleic acid sample. The detection probe 5 comprises, from the 5' end, two stem portions 5c and 5d which form a complementary strand, a loop portion 5e which is a region between the two stem portions 5c and 5d and labeled with a labeling substance, and a sequence 5b capable of hybridizing to the second portion. That is to say, the detection probe 5 has 3' protruding end. In addition, the detection probe of the present embodiment may have 5' protruding end. In this case, the detection probe of the present embodiment has a sequence capable of hybridizing to the second portion at the 3' terminal region.

In addition, from the viewpoint of the ability of strictly distinguishing and recognizing similar miRNA, a label of the loop portion is preferably related to the base sequence of the second portion.

Furthermore, the target nucleic acid of the detection probe 5 is preferably miRNA.

Figure 3:
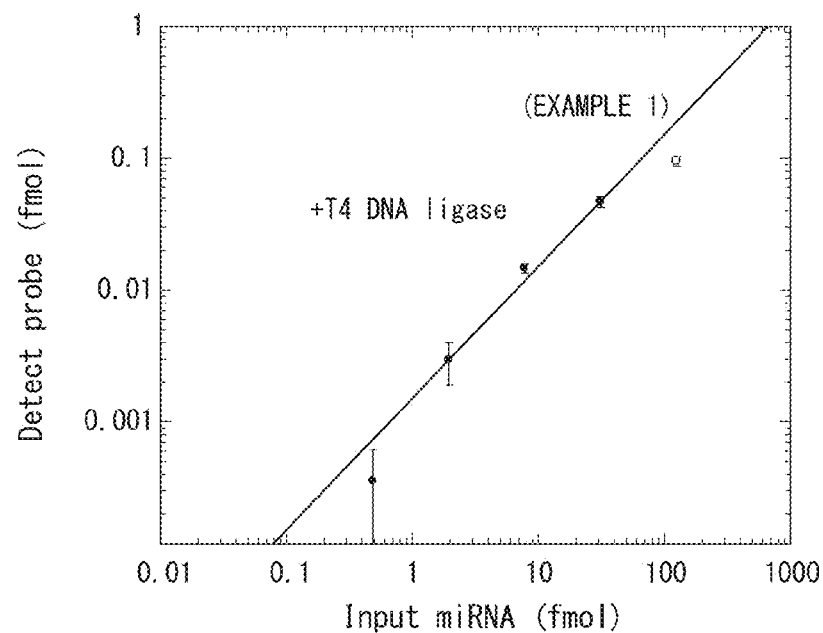
FIG. 3 is a quantitative result of miRNA in Example 1.

The detection probe 5 may be labeled with a single labeling substance, and as shown in FIG. 3, the detection probe 5 may be labeled with a plurality of labeling substances 5a1 and 5a2. The labeling substances 5a1 and 5a2 may be the same substance, and may be the different substances.

When the same substance is used as the labeling substance 5a1 and 5a2, it is possible to raise the intensity of the label, and to detect the target miRNA with higher sensitively.

In addition, when the different substances are used as the labeling substances 5a1 and 5a2, it is possible to confirm existence or non-existence of the formation of the stem-loop structure of the detection probe based on FRET, for example, by using a combination of labeling substances by which FRET can occur.

The detection probe set of the present embodiment is a detection probe set comprising plural kinds of detection probes used to detect a nucleic acid comprising plurali kinds of first portions and second portions in a nucleic acid sample. In the detection probe of the present embodiment described above, each loop portion is labeled with different kinds of labeling substances, and the label of the loop portion and the base sequence of the second portion are related in these plural kinds of detection probes.

In addition, the target nucleic acid of the detection probe set of the present embodiment is preferably miRNA.

As described above, among the plural miRNAs to be detected, there are plural miRNAs in which the base sequence of the first portion constituting miRNA is the same.

According to the detection probe set of the present embodiment, since the sequence information (the base sequence of the second portion) of the target miRNA recognized by the detection probes constituting the detection probe set is related to different kinds of labels, it is possible to exactly identify each miRNA.

<<Method for Detecting Nucleic Acid>>

First Embodiment

A method for detecting nucleic acid of the present embodiment comprises:
  (a) a step of contacting a solution comprising:
    a nucleic acid sample containing a nucleic acid comprising a first portion and a second portion, and
    a detection probe labeled with a labeling substance containing a sequence which forms a stem-loop structure and is capable of hybridizing to the second portion, and having 5' protruding end or 3' protruding end,
  with a substrate fixed with a capture probe containing a sequence capable of hybridizing to the first portion,
  (b) a step of forming the nucleic acid—the detection probe—the capture probe complex on the substrate by hybridizing the second portion to the detection probe and hybridizing the first portion to the capture probe,
  (c) a step of hybridizing the first portion to the capture probe and ligating an end of the detection probe and ends of the nucleic acid and the capture probe,
  (d) a step of detecting the labeling substance of the nucleic acid—the detection probe—the capture probe complex formed on the substrate.

Each step in the method for detecting nucleic acid of the present embodiment is the same as each step of the <<Method for detecting nucleic acids>> described above, explanation thereof will be omitted.

Second Embodiment

A method for detecting nucleic acid of the present embodiment comprises:
  (a') a step of contacting a nucleic acid sample containing a nucleic acid comprising a first portion and a second portion with a substrate fixed with a capture probe containing a sequence capable of hybridizing to the first portion,
  (b') a step of hybridizing the second portion to a detection probe by contacting the detection probe labeled with a labeling substance containing a sequence which forms a stem-loop structure and is capable of hybridizing to the second portion and having 5' protruding end or 3' protruding end, with the substrate, and forming the nucleic acid—the detection probe—the capture probe complex on the substrate by hybridizing the first portion to the capture probe, (c) a step of hybridizing the first portion to the capture probe and ligating an end of the detection probe and ends of the nucleic acid and the capture probe, (d) a step of detecting the labeling substance of the nucleic acid—the detection probe—the capture probe complex formed on the substrate.

In the method for detecting nucleic acid of the present embodiment, first, after contacting a nucleic acid sample with the substrate to which the capture probe is fixed, contacting the detection probe with the substrate. With regard to other steps, they are the same as the method for detecting nucleic acid according to the first embodiment.

According to the method for detecting miRNA in the present embodiment, since bridging probe required conventionally is unnecessary, the operation is simplified. Furthermore, since there is no need to label miRNA itself with a labeling substance, it is possible to detect the target miRNA with high sensitivity.

Hereinafter, explanation of the present invention is provided by the following examples. However, the present invention is not limited to the following examples.

EXAMPLES

Example 1

Synthesis of Target miRNA, Capture Probe, and Detection Probe

RNA having the sequence of miR-141 was synthesized as the target miRNA. In addition, two kinds of the nucleic acid probes, the capture probe and the detection probe having complementary sequence to the above RNA were designed and synthesized.

The sequences used for the target miRNA, the capture probe, and the detection probe are shown below.

(1) Target miRNA: miR-141

(SEQ ID NO 1: 22 mer)
[SEQ: 5'-UAACACUGUCUGGUAAAGAUGG-3']

(2) Capture Probe 1 (Capture Probe 1)

(SEQ ID NO: 29)
[SEQ: 5'-p-X1-fS-3']

X1 represents the following sequence, p represents a phosphate, S represents a thiol group, f represents a 6-FAM (6-fluorescein).

(SEQ ID NO 2: 35 mer)
X1: ACCAGACAGTGTTAACAACAACAACAAGAACAACA (3) Detection Probe 1 (Detect Probe 1)

(SEQ ID NO: 30)
[SEQ: 5'-p-X2-A1-X3-3']

X2, X3 represent the following sequences, p represents a phosphate, A1 represents an Alexa647-AminoC6-dA.

(SEQ ID NO 3: 17 mer)
X2: CTCAACTGGTGTCGTGG (SEQ ID NO 4: 26 mer)
X3: GTCGGCAATTCAGTTGAGCCATCTTT By using an ink jet device (MicroJet Co, LaboJet-500Bio), a microarray was prepared by discharging a solution containing a capture probe shown in Table 1 onto a glass substrate.

In Table 1, the composition of 20×SSC buffer is 3 M NaCl, 0.3 M sodium citrate.

TABLE 1

| 10 µM Capture probe 1 | 45 µl |
| 5M betaine | 22.5 µl |
| 20 × SSC buffer | 22.5 µl |
| Milli-Q Water | 60 µl |
| Total | 150 µl |

Furthermore, the hybridization reaction solution containing arbitrary concentration of miR-141 and the detection probe was prepared as shown in Table 2.

TABLE 2

| X pM miR-141 | 100 µl |
| 20 µM Detect probe 1 | 0.75 µl |
| 1M Tris—HCl (pH 7.5) | 20 µl |
| 1M MgCl$_2$ | 3 µl |
| 100 mM ATP | 0.3 µl |
| 10 mg/ml BSA | 3 µl |
| 1M DTT | 3 µl |
| 2.5M NaCl | 18 µl |
| 50% PEG6000 (Hampton Research) | 60 µl |
| RNase-free water | 92 µl |
| Total | 300 µl |

The hybridization reaction solution was incubated at 95° C. for 5 minutes and returned to room temperature. Then T4 DNA ligase was added to a final concentration of 5 units/µl. Then the hybridization reaction solution was sealed in a state of contacting with the microarray substrate, hybridization was carried out at 30° C. or 2 hours while being shaken at a speed of 1000 rpm on a shaker.

After the hybridization reaction was completed, the microarray substrate was washed in 0.2×SSC buffer (30 mM NaCl, 3 mM sodium citrate) by shaking for 10 minutes, and this washing operation was repeated twice. The substrate was subsequently dried, observed with a fluorescence microscope, and the fluorescence intensity was measured.

The results are shown in FIG. 3. In each spot with a fixed probe, the fluorescence image of the detection probe labeled with Alexa647 were observed, and linearity was observed in a range of number of molecules 0.5 fmol to 50 fmol of miR-141 used for the hybridization reaction. Thus, it was confirmed that the signal of fluorescence intensity over the spots is increased depending on the concentration of miRNA.

Example 2

Synthesis of Target miRNA, Capture Probe, and Detection Probe

RNA having the sequence of miR-143 was synthesized as another target miRNA. In addition, two kinds of the nucleic acid probes, the capture probe and the detection probe having complementary sequence to the above RNA were designed and synthesized.

The sequences used for the target miRNA, the capture probe, and the detection probe are shown below.

(1) Target miRNA: miR-143

(SEQ ID NO 5: 21 mer)
[SEQ: 5'-UGAGAUGAAGCACUGUAGCUC-3']

(2) Capture Probe 2 (Capture Probe 2)

(SEQ ID NO: 31)
[SEQ: 5'-p-X4-fS-3']

X4 represents the following sequence, p represents a phosphate, S represents a thiol group, f represents a 6-FAM (6-fluorescein).

(SEQ ID NO 6: 34 mer)
X4: GTGCTTCATCTCAACAACAACAACAACAACAACA (3) Detection Probe 2 (Detect Probe 2)

(SEQ ID NO: 32)
[SEQ: 5'-p-X5-A1-X6-3']

X5, X6 represent the following sequences, p represents a phosphate, Al represents an Alexa647-AminoC6-dA.

(SEQ ID NO 7: 17 mer)
X5: CTCAACTGGTGTCGTGG (SEQ ID NO 8: 26 mer)
X6: GTCGGCAATTCAGTTGAGGAGCTACA The microarray was prepared, hybridization was carried out and the fluorescence intensity over the spots on the substrate was measured in the same manner as described in Example 1.

Comparative Example 1

Except that T4 DNA ligase was not added in Example 2, the microarray was prepared, hybridization was carried out and the fluorescence intensity over the spots on the substrate was measured in the same manner as described in Example 2.

Figure 4:
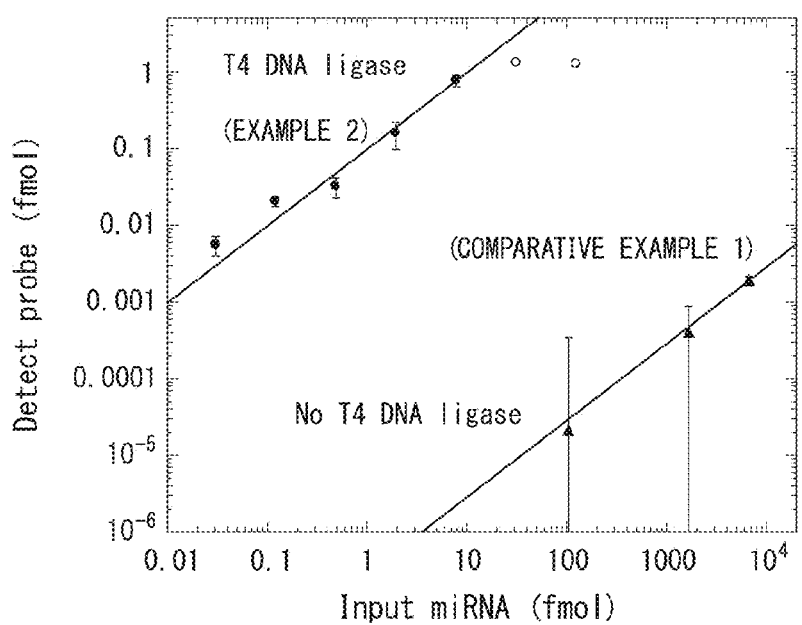
FIG. 4 is a quantitative result of miRNA in Example 2.
Figure 5:
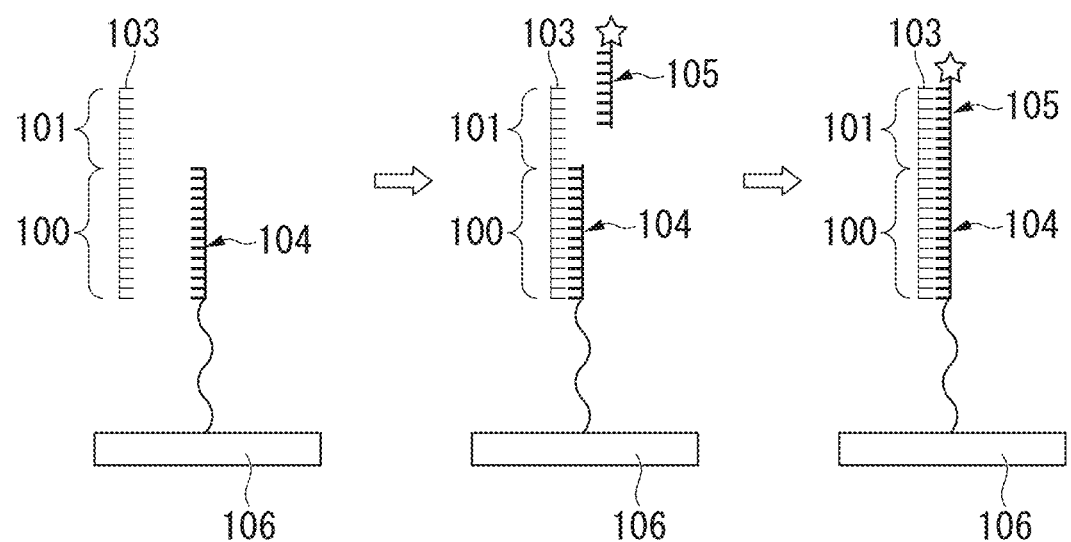
FIG. 5 is a schematic view of one embodiment of a conventional method for quantifying nucleic acids.
Figure 6:
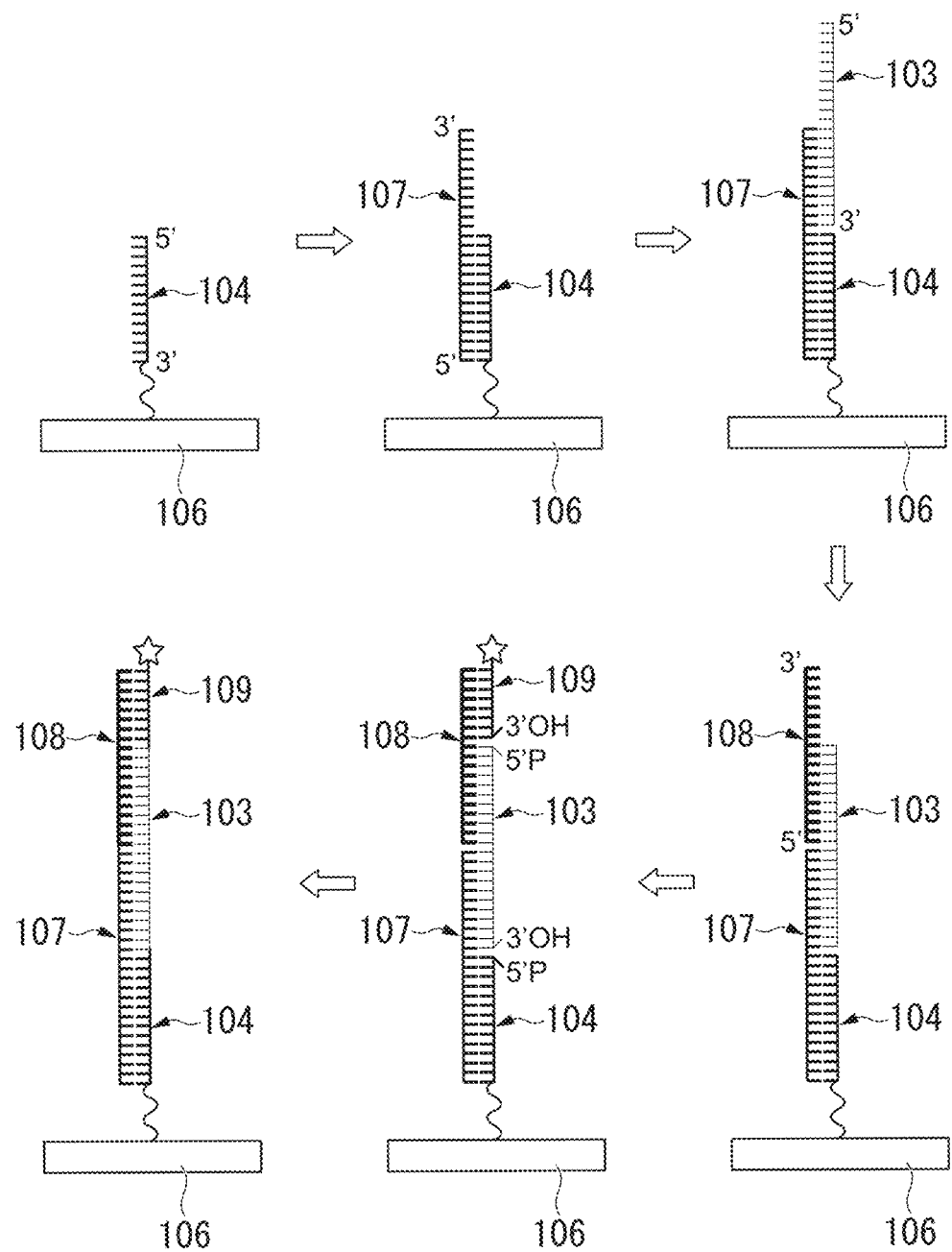
FIG. 6 is a schematic view of one embodiment of a conventional method for quantifying nucleic acids.

The results of Example 2 and Comparative Example 1 are shown in FIG. 4. In Example 2, and linearity was observed in a range of number of molecules 0.03 fmol to 10 fmol of miR-143 used for the hybridization reaction. On the other hand, in Comparative Example 1 in which T4 DNA ligase was not used, the detection sensitivity was reduced to about $1/10^5$. Accordingly, it is confirmed that the detection sensitivity significantly increases by ligating the target miRNA, the capture probe, and the detection probe.

Example 3

Synthesis of Target miRNA, Capture Probe, and Detection Probe

RNA having the sequence of miR-141 and miR-200a was synthesized as the similar target miRNAs. In addition, a total three kinds of the nucleic acid probes, one kind of the capture probe and two kinds of the detection probes having complementary sequence to the above RNA were designed and synthesized.

The sequences used for the target miRNA, the capture probe, and the detection probe are shown below.

(1) Target miRNA: miR-141

(SEQ ID NO 1: 22 mer)
[SEQ: 5'-UAACACUGUCUGGUAAAGAUGG-3']

(2) Target miRNA: miR-200a (SEQ ID NO 9: 22 mer)
[SEQ: 5'-UAACACUGUCUGGUAACGAUGU-3']

(3) Capture Probe 1 (Capture Probe 1)

(SEQ ID NO: 29)
[SEQ: 5'-p-X1-fS-3']

X1 represents the following sequence, p represents a phosphate, S represents a thiol group, f represents a 6-FAM (6-fluorescein).

(SEQ ID NO 2: 35 mer)
X1: ACCAGACAGTGTTAACAACAACAACAACAACAACA (4) Detection Probe 1 (Detect Probe 1)

(SEQ ID NO: 30)
[SEQ: 5'-p-X2-A1-X3-3']

X2, X3 represent the following sequences, p represents a phosphate, Al represents an Alexa647-AminoC6-dA.

(SEQ ID NO 3: 17 mer)
X2: CTCAACTGGTGTCGTGG (SEQ ID NO 4: 26 mer)
X3: GTCGGCAATTCAGTTGAGCCATCTTT (5) Detection Probe 3 (Detect Probe 3)

(SEQ ID NO: 33)
[SEQ: 5'-p-X2-A1-X7-3']

X2, X7 represent the following sequences, p represents a phosphate, Al represents an Alexa647-AminoC6-dA.

(SEQ ID NO 3: 17 mer)
X2: CTCAACTGGTGTCGTGG (SEQ ID NO 10: 26 mer)
X7: GTCGGCAATTCAGTTGAGACATCGTT The microarray was prepared in the same manner as described in Example 1.

Furthermore, the hybridization reaction solution containing miR-141 or miR-200a, the detection probe 1 and the detection probe 3 was prepared as shown in Table 3.

TABLE 3

| | |
|---|---|
| 300 pM miR-141 or miR-200a | 100 μl |
| 20 μM Detect probe 1 | 0.75 μl |
| 20 μM Detect probe 3 | 0.75 μl |

TABLE 3-continued

| | |
|---|---|
| 1M Tris—HCl (pH 7.5) | 20 μl |
| 1M MgCl$_2$ | 3 μl |
| 100 mM ATP | 0.3 μl |
| 10 mg/ml BSA | 3 μl |
| 1M DTT | 3 μl |
| 2.5M NaCl | 18 μl |
| 50% PEG6000 (Hampton Research) | 60 μl |
| RNase-free water | 92 μl |
| Total | 300 μl |

Hybridization was carried out and the fluorescence intensity over the spots on the substrate was measured in the same manner as described in Example 1.

The results are shown in Table 4. In each spot with a fixed probe, each fluorescence image of the detection probe which is labeled with Alexa647 or Alexa532 was observed, and miR-141 and miR-200a were quantified from the fluorescence intensity. Assuming that the fluorescence intensity of the detection probe having a sequence that is fully complementary to the target miRNA is 100%, the fluorescence intensity becomes 1% or less in the presence of miRNA having a sequence with different 2 bases. Accordingly, it as confirmed that the detection probe has high specificity.

TABLE 4

| | | synthetic miRNAs | |
|---|---|---|---|
| | | miR-141 | miR-200a |
| Detect Probes | miR-141 | 100 | 0.58 |
| | miR-200a | 0.69 | 100 |

Example 4

Synthesis of Target miRNA, Capture Probe, and Detection Probe

RNA having the sequence of let-7a was synthesized as the target miRNA. In addition, a total three kinds of the nucleic acid probes, two kinds of capture the probes and the detection probe having complementary sequence to the above RNA, but their lengths are different, were designed and synthesized.

The sequences used for the target miRNA, the capture probe, and the detection probe are shown below.

(1) Target miRNA: Let-7a (SEQ ID NO 11: 22 mer)
[SEQ: 5'-UGAGGUAGUAGGUUGUAUAGUU-3']

(2) Capture Probe 3 (Capture Probe 3)

(SEQ ID NO: 34)
[SEQ: 5'-p-X9-fS-3']

X9 represents the following sequence, p represents a phosphate, S represents a thiol group, f represents a 6-FAM (6-fluorescein).

(SEQ ID NO 12: 35 mer)
X9: AACCTACTACCTCAACAACAACAACAACAACAACA (3) Capture Probe 4 (Capture Probe 4)

(SEQ ID NO: 35)
[SEQ: 5'-p-X10-fS-3']

X10 represents the following sequence, p represents a phosphate, S represents a thiol group, f represents a 6-FAM (6-fluorescein).

(SEQ ID NO 13: 34 mer)
X10: ACCTACTACCTCAACAACAACAACAACAACAACA (4) Detection Probe 4 (Detect Probe 4)

(SEQ ID NO: 36)
[SEQ: 5'-p-X11-A1-X12-3']

X11, X12 represent the following sequences, p represents a phosphate, A1 represents an Alexa647-AminoC6-dA.

(SEQ ID NO 14: 17 mer)
X11: CTCAACTGGTGTCGTGG (SEQ ID NO 15: 26 mer)
X12: GTCGGCAATTCAGTTGAGAACTATAC

TABLE 5

| | |
|---|---|
| 300 nM let-7a | 100 μl |
| 20 μM Capture probe 3 or 20 μM Capture probe 4 | 0.75 μl |
| 20 μM Detect probe 4 | 0.75 μl |
| 1M Tris—HCl (pH 7.5) | 20 μl |
| 1M MgCl$_2$ | 3 μl |
| 100 mM ATP | 0.3 μl |
| 10 mg/ml BSA | 3 μl |
| 1M DTT | 3 μl |
| 2.5M NaCl | 18 μl |
| 50% PEG6000 (Hampton Research) | 60 μl |
| RNase-free water | 92 μl |
| Total | 300 μl |

The hybridization reaction solution was incubated at 95° C. for 5 minutes and returned to room temperature. Then T4 DNA ligase was added to a final concentration of 5 units/μl. Then the hybridization reaction was carried out at 30° C. for 2 hours.

After the hybridization reaction was completed, denaturing urea acrylamide gel electrophoresis was carried out, and it was confirmed that the ternary complex of the capture probe-detection probe 4-let-7a was formed.

Figure 8:
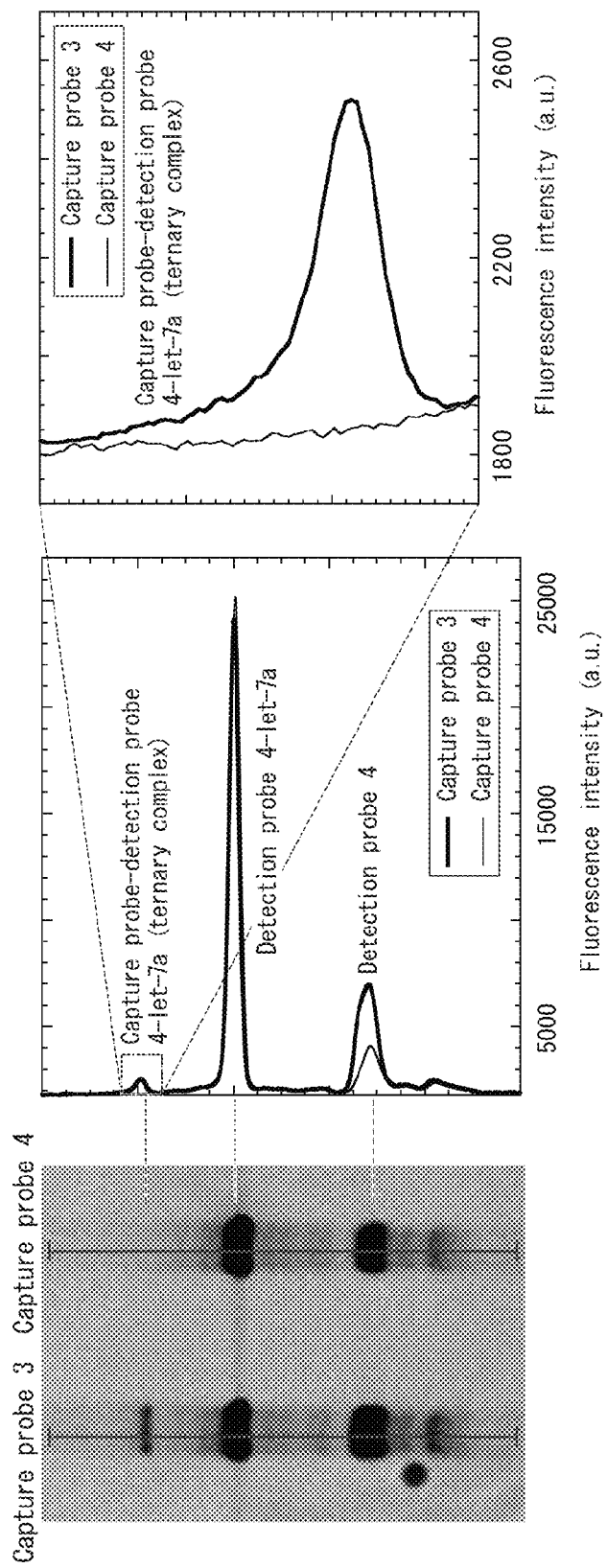
FIG. 8 is a result of electrophoresis in Example 4.

The results are shown in FIG. 8. A photograph of the gel after the electrophoresis was taken by setting the fluorescence of Alexa647 bound to the detection probe 4 as an indicator. As a result, a band of the ternary complex was observed at a position of approximately 130 bases in length when the capture probe 3 is contained. On the other hand, since a signal did not appear at all when the capture probe 4 is contained, it was shown that it is possible to control the formation of the ternary complex by changing the base length of the capture probe. That is to say, when the capture probes 3 and 4 are fixed to different regions on the substrate, the signals of let-7a and let-7b are detected in the different regions from each other. As described above, according to the present embodiment, a group of similar miRNAs can be quantified specifically.

Example 5

Figure 9:
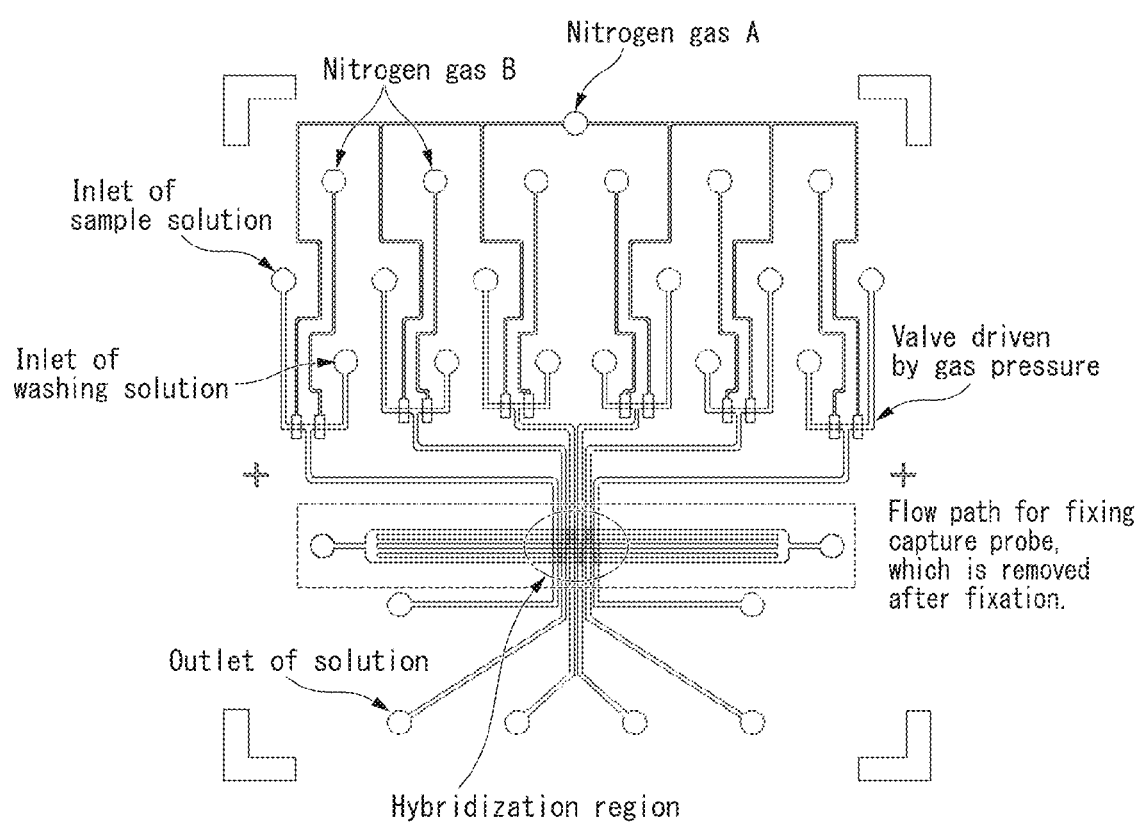
FIG. 9 is a schematic view of a microchip in Example 5.

The microchip shown in FIG. 9 was prepared with PDMS (Polydimethylsiloxane), by using the reagent of Example 1, quantification of miRNA on the microchip was attempted. In each flow path, width is 200 μm and height is 20 μm, and two solution inlets are arranged, and each flow path is separated by a valve which is opened and closed by the gas pressure. Such flow path sets are arranged in six parallel rows on the glass substrate of 30 mm square.

Figure 10:
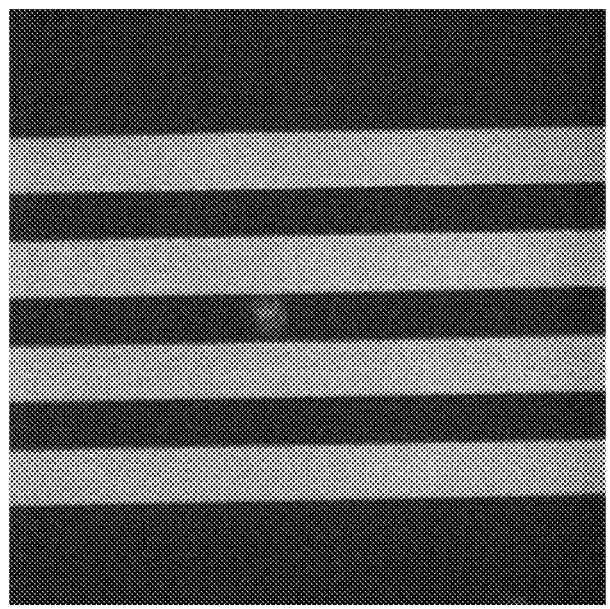
FIG. 10 is a fluorescence image of the detection probe fixed on a glass substrate in Example 5.

First, flow path for fixing the capture probe (flow path made of PDMS surrounded by a dashed box) was fixed on a glass substrate, and FAM-labeled capture probe solution was introduced from one inlet, and fixed on a glass substrate. Then the flow path was washed, and the flow path was removed. As a result, it as possible to fix the detection probes lineally, as shown in FIG. 10.

Figure 11:
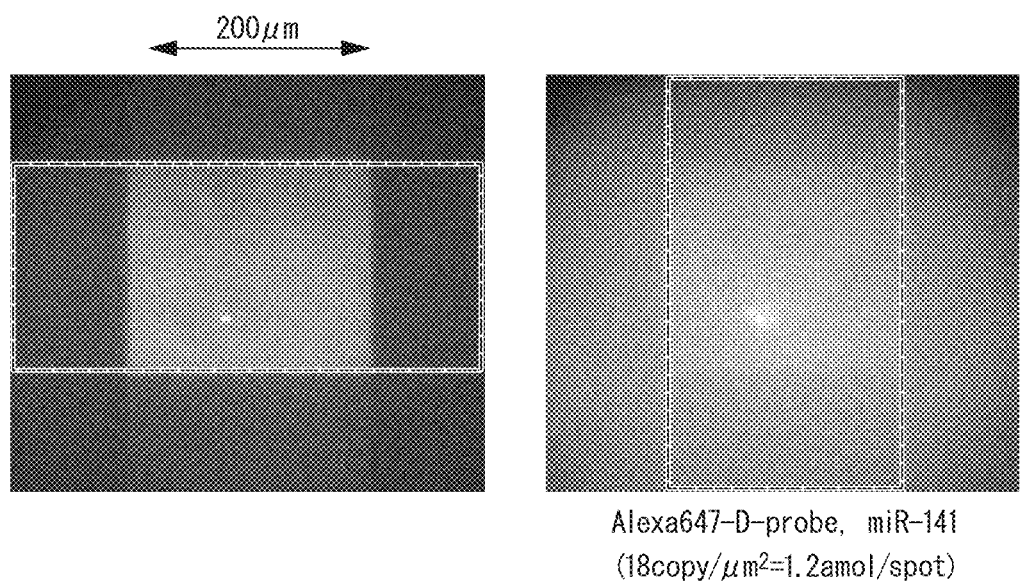
FIG. 11 is a fluorescence image of the capture probe or the detection probe fixed on a glass substrate in Example 5.

Subsequently, flow path for hybridization was affixed to the glass substrate obtained by removing the flow path for fixing the capture probe, sample solution (containing 25 nM miR-141, 100 nM detection probe labeled with Alexa647, and T4 DNA ligase, etc.) was introduced with a syringe pump from "sample solution inlet" while closing the valve of the flow path for washing solution by "nitrogen gas B" (flow rate: 0.8 μl/min, 10 minutes). Then the washing solution was flushed by switching the valve, and the amount of the detection probe labeled with Alexa647 bound on the region fixed with the capture probe was measured. Results are shown in FIG. 11. At the intersection with the capture probe fixed on the dashed line portion shown in the left figure of FIG. 11, miRNA and the detection probe are bound predominantly which have flowed through the dashed line portion shown the right figure of FIG. 11, and it is confirmed that the method of quantifying miRNA of this embodiment is also applicable when using the microchannel.

From the above results, according to this embodiment, it is clear that it is possible to easily quantify nucleic acids with high accuracy and high sensitivity.

INDUSTRIAL APPLICABILITY

It is possible to provide a method for detecting nucleic acid which is capable of detecting the nucleic acid with simplicity, high accuracy and high sensitivity, and a detection probe and detection probe set used in the method for detecting nucleic acids.

What is claimed is:

1. A method for detecting a target nucleic acid, comprising:
   (a) contacting a nucleic acid sample comprising a target nucleic acid, comprising a first portion and a second portion, with:
      (i) a detection probe, wherein the detection probe is labeled with a labeling substance and comprises a nucleic acid sequence that forms a stem-loop structure and having a 5' protruding end or a 3' protruding end that is capable of hybridizing to the second portion, and
      (ii) a capture probe comprising a nucleic acid sequence capable of hybridizing to the first portion, wherein the capture probe is immobilized to a substrate, under conditions to form a target nucleic acid-detection probe-capture probe complex by hybridizing the second portion to the detection probe and hybridizing the first portion to the capture probe;
   (b) ligating a first end of the detection probe with an end of the target nucleic acid and ligating a second end of the detection probe with an end of the capture probe; and
   (c) detecting the labeling substance of the nucleic acid-detection probe-capture probe complex formed on the substrate.

2. The method for detecting a target nucleic acid according to claim 1, wherein the nucleic acid sample comprising the target nucleic acid is contacted with the detection probe in a solution.

3. The method for detecting a target nucleic acid according to claim 1, wherein the target nucleic acid is contacted with the detection probe after the target nucleic acid is contacted with the capture probe.

4. The method for detecting a target nucleic acid according to claim 1, wherein the target nucleic acid is contacted with the capture probe after the target nucleic acid is contacted with the detection probe.

5. The method for detecting a target nucleic acid according to claim 1, wherein the method further comprises a step of quantifying the target nucleic acid by quantitatively detecting the labeling substance of the nucleic acid-detection probe-capture probe complex formed on the substrate.

6. The method for detecting a target nucleic acid according to claim 1, wherein a plurality of detection probes is employed to detect a plurality of different target nucleic acids in the nucleic acid sample, wherein the detection probes are labeled with a labeling substance that is different for each different target nucleic acid detected.

7. The method for detecting a target nucleic acid according to claim 1, wherein the 5' end or the 3' end of the capture probe is immobilized to the substrate.

8. The method for detecting a target nucleic acid according to claim 1, wherein the target nucleic acid is contacted with a plurality of detection probes having varying base lengths and a plurality of capture probes having varying base lengths.

9. The method for detecting a target nucleic acid according to claim 1, wherein step (a) and step (b) are performed simultaneously.

10. The method for detecting a target nucleic acid according to claim 1, wherein the capture probe and/or the detection probe contain a LNA (Locked Nucleic Acid) or a BNA (Bridged Nucleic Acid).

11. The method for detecting a target nucleic acid according to claim 1, wherein the target nucleic acid is a short chain RNA.

12. The method for detecting a target nucleic acid according to claim 1, wherein the target nucleic acid is miRNA.

13. The method for detecting a target nucleic acid according to claim 1, wherein the first portion of the target nucleic acid is about 5 to 17 bases.

14. The method for detecting a target nucleic acid according to claim 1, wherein the second portion of the target nucleic acid is about 5 to 17 bases.

* * * * *